US009082215B2

(12) United States Patent
Hannula

(10) Patent No.: US 9,082,215 B2
(45) Date of Patent: Jul. 14, 2015

(54) METHOD OF AND SYSTEM FOR OVERLAYING NBS FUNCTIONAL DATA ON A LIVE IMAGE OF A BRAIN

(75) Inventor: Henri Hannula, Helsinki (FI)

(73) Assignee: Nexstim Oy, Helsinki (FI)

( * ) Notice: Subject to any disclaimer, the term of this patent is extended or adjusted under 35 U.S.C. 154(b) by 134 days.

(21) Appl. No.: 13/823,739

(22) PCT Filed: Jun. 4, 2012

(86) PCT No.: PCT/FI2012/050551
§ 371 (c)(1),
(2), (4) Date: Mar. 15, 2013

(87) PCT Pub. No.: WO2012/164173
PCT Pub. Date: Dec. 6, 2012

(65) Prior Publication Data
US 2013/0176336 A1    Jul. 11, 2013

Related U.S. Application Data

(60) Provisional application No. 61/492,821, filed on Jun. 3, 2011, provisional application No. 61/564,336, filed on Nov. 29, 2011.

(51) Int. Cl.
*G06T 19/00* (2011.01)
*A61B 5/00* (2006.01)
*A61B 5/0488* (2006.01)
(Continued)

(52) U.S. Cl.
CPC ............. *G06T 19/006* (2013.01); *A61B 5/0042* (2013.01); *A61B 5/0488* (2013.01);
(Continued)

(58) Field of Classification Search
CPC ..................................................... G06T 19/006
USPC .................................................. 345/629, 633
See application file for complete search history.

(56) References Cited

U.S. PATENT DOCUMENTS 6,849,040 B2    2/2005   Ruohonen et al.
7,440,789 B2    10/2008  Hannula et al.
(Continued)

FOREIGN PATENT DOCUMENTS

WO    WO 2008031847 A1    3/2008
WO    WO 2012117166 A1    9/2012

OTHER PUBLICATIONS

Kosaka et al., "Augmented Reality System for Surgical Navigation Using Robust Target Vision"; Advanced Technology Research Center Olympus Optical Co., Ltd., IEEE 2000 pp. 1-8.*

*Primary Examiner* — Maurice L McDowell, Jr.
(74) *Attorney, Agent, or Firm* — Seppo Laine Oy

(57) ABSTRACT

The present invention discloses a method of overlaying Navigated Brain Stimulation (NBS) functional data on a live image of a brain. The method comprises the steps of obtaining a live image of a brain, obtaining a functional map of the brain comprising an anatomical model of the brain and NBS functional data associated with the brain, identifying at least one anatomical landmark of the brain from the live image of the brain, identifying at least one of said identified anatomical landmarks on the anatomical model of the brain, modifying the functional map so that the identified at least one anatomical landmark of the model corresponds in size and orientation to the corresponding at least one anatomical landmark in the live image of the brain, and digitally overlaying at least said NBS functional data on said live image of the brain according to the corresponding, aligned anatomical landmarks.

16 Claims, 14 Drawing Sheets

(51) Int. Cl.
*A61N 2/00* (2006.01)
*A61B 5/055* (2006.01)
*A61B 19/00* (2006.01)

(52) U.S. Cl.
CPC ........... *A61B5/7425* (2013.01); *A61B 19/5225* (2013.01); *A61N 2/006* (2013.01); *A61B 5/055* (2013.01); *A61B 19/56* (2013.01); *A61B 2019/5265* (2013.01); *A61B 2019/5291* (2013.01)

(56) References Cited

U.S. PATENT DOCUMENTS

| | | |
|---|---|---|
| 7,720,519 B2 | 5/2010 | Ruohonen |
| 2005/0075560 A1 | 4/2005 | Hannula et al. |
| 2008/0058581 A1 | 3/2008 | Aho |
| 2008/0058582 A1 | 3/2008 | Aho et al. |
| 2008/0262338 A1 | 10/2008 | Paitel et al. |

* cited by examiner

METHOD OF AND SYSTEM FOR OVERLAYING NBS FUNCTIONAL DATA ON A LIVE IMAGE OF A BRAIN

FIELD OF THE INVENTION

This invention relates to a method and system for overlaying Navigated Brain Stimulation (NBS) functional data on a live image of a brain. In particular, a functional map comprising the brain's NBS functional data and an anatomical model of the brain is constructed before surgery, so that during surgery anatomical landmarks on the anatomical model may be aligned with corresponding anatomical landmarks on the live image of the brain.

BACKGROUND TO THE INVENTION

In modern brain surgery, surgeons often use optical microscopes and/or specialized imaging devices to view the brain. There has, however, been a long felt need for a highly accurate and timely manner of displaying local brain functions to a surgeon. At present, methods which are accurate require significant amounts of time at the beginning of an operation, which pose an increased risk to the patient. Conversely, methods which require less time during the operation to configure are less accurate and pose corresponding risks.

When operating in a brain, it is vital for a surgeon to know which portions of the brain in the operation site are eloquent areas, the removal of which will result in loss of motor function, sensory function, language function, vision etc. Currently, a common method for determining these local brain functions is to physically stimulate a plurality of locations of an exposed brain, normally in the form of a grid, with a probe delivering a short pulse of electric current, and then determining if there is a corresponding visual or measureable response from the patient. When a response is elicited, then that point in the brain is tagged as a functional point. If no response is elicited, then that point is deemed safe to cut through.

More recently, prior to an operation, a patient may undergo NBS for functional mapping. The extent of the mapping can be determined based on the particulars of the impending operation. For example, in the case where a tumor is to be removed from a patient's brain, the NBS functional mapping can be restricted to mapping the functions of the brain within the immediate vicinity of the tumor. In the case of an exploratory or more invasive surgery, the functional mapping can be more extensive.

NBS functional mapping is a non-invasive method of accurately mapping a patient's brain functions through the use of navigated Transcranial Magnetic Stimulation (TMS). By applying an electro-magnetic stimulation to a location on, or within, a patient's brain, and measuring and/or determining a patient's corresponding response, it is possible to provide an accurate 2- or 3-dimensional map of the patient's brain in a non-sterile environment. More detailed descriptions of 2-dimensional and 3-dimensional NBS functional mapping can be found, for example, in US 2008/058582, "Transcranial magnetic stimulation induction coil device with attachment portion for receiving tracking device", US 2005/075560, "Stereotactic frame and method for supporting a stereotactic frame", U.S. Pat. No. 7,720,519, "Method for three-dimensional modeling of the skull and internal structures thereof", U.S. Pat. No. 11/853,232, "A method for visualizing electric fields on the human cortex for the purpose of navigated brain stimulation", U.S. Pat. No. 11/853,256, "Improved accuracy of navigated brain stimulation by online or offline corrections to co-registration", US 2008/058582, "Transcranial magnetic stimulation induction coil device with attachment portion for receiving tracking device", US 2008/058581, "Transcranial magnetic stimulation induction coil device and method of manufacture", U.S. Pat. No. 6,849,040, "Method and apparatus for dose computation of magnetic stimulation", U.S. Pat. No. 7,440,789, "Electrode structure for measuring electrical responses from the human body", all of which are herein incorporated by reference.

As is described in more detail in at least some of the above mentioned references, at the beginning of, or prior to, NBS functional mapping, a model of the patient's brain is obtained or selected for mapping. Although a number of options are available, as described therein, according to an embodiment of the present invention, an MRI or a CT of the patient's brain is utilized as the anatomical model for mapping. Once the MRI data has been compiled, then through knowing the exact location and orientation of the patient's head and each TMS pulse, it is possible to accurately map the functions of the patient's brain to the anatomical model.

SUMMARY OF THE INVENTION

According to a first aspect of the invention there is provided a method of overlaying Navigated Brain Stimulation (NBS) functional data on a live image of a brain.

According to certain embodiments of the present invention, there are methods described herein comprising some, or all, of the following steps; obtaining a live image of a brain, obtaining a functional map of the brain comprising an anatomical model of the brain and NBS functional data associated with the brain, identifying at least one anatomical landmark of the brain from the live image of the brain, identifying at least one of said identified anatomical landmarks on the anatomical model of the brain, modifying the functional map so that the identified at least one anatomical landmark of the model corresponds in size and orientation to the corresponding at least one anatomical landmark in the live image of the brain, and digitally overlaying at least said NBS functional data on said live image of the brain according to the corresponding, aligned anatomical landmarks.

Furthermore, according to certain embodiments the method comprises the further steps of; continuously tracking said identified anatomical landmarks, and continuously updating the digitally overlaid NBS functional data to ensure that the identified anatomical landmarks of the functional map remain superimposed over the corresponding anatomical landmarks of the live image.

Still yet, according to certain embodiments, the method further comprises the steps of; determining a change in distance between at least two anatomical landmarks from the live image, and determining a reliability indication for the location of the NBS functional data based on said determined change in distance.

Advantageously, the method comprises the step of displaying said reliability indication graphically.

Alternatively, or in addition, the method comprises the steps of taking a freeze frame from the live image, identifying said anatomical landmarks from said freeze frame, digitally overlaying said modified functional map on said freeze frame, determining any changes between said freeze frame and said live image, and updating the overlay of the at least NBS functional data and the live image based on said determined changes.

According to certain embodiments, the method comprises the step of modifying the transparency of at least a portion of the functional map. In an example version, only the transparency of the anatomical model portion of the functional map is adjusted.

The step of modifying the functional map may include at least one of the steps of; zooming, panning, tilting, adjusting, orienting and moving.

According to certain embodiments, the method further comprises displaying the functional map and the live image of the brain on a screen; and providing a GUI to enable an operator to modify the functional map so as to/align the identified at least one anatomical landmark of the model and the at least one anatomical landmark in the live image of the brain.

According to a second aspect of the invention there is provided a computer program product stored on a computer readable medium for causing a processer to perform some or all of the steps of; identifying at least one anatomical landmark of a brain from a live image of the brain, identifying at least one of said identified anatomical landmarks on a functional map of the brain, the functional map comprising an anatomical model of the brain and NBS functional data associated with the brain, modifying the functional map so that the identified at least one anatomical landmark of the model corresponds in size and orientation to those of the live image of the brain, and digitally overlaying at least said modified NBS functional data on said live image of the brain according to the corresponding, aligned anatomical landmarks.

According to a third aspect of the invention there is provided a processor of a computing device arranged to perform at least some of the method steps defined above.

BRIEF DESCRIPTION OF THE DRAWINGS

The invention will be described, by way of example only, with reference to the accompanying drawings in which.

DETAILED DESCRIPTION OF EXEMPLARY EMBODIMENTS

Figure 1:
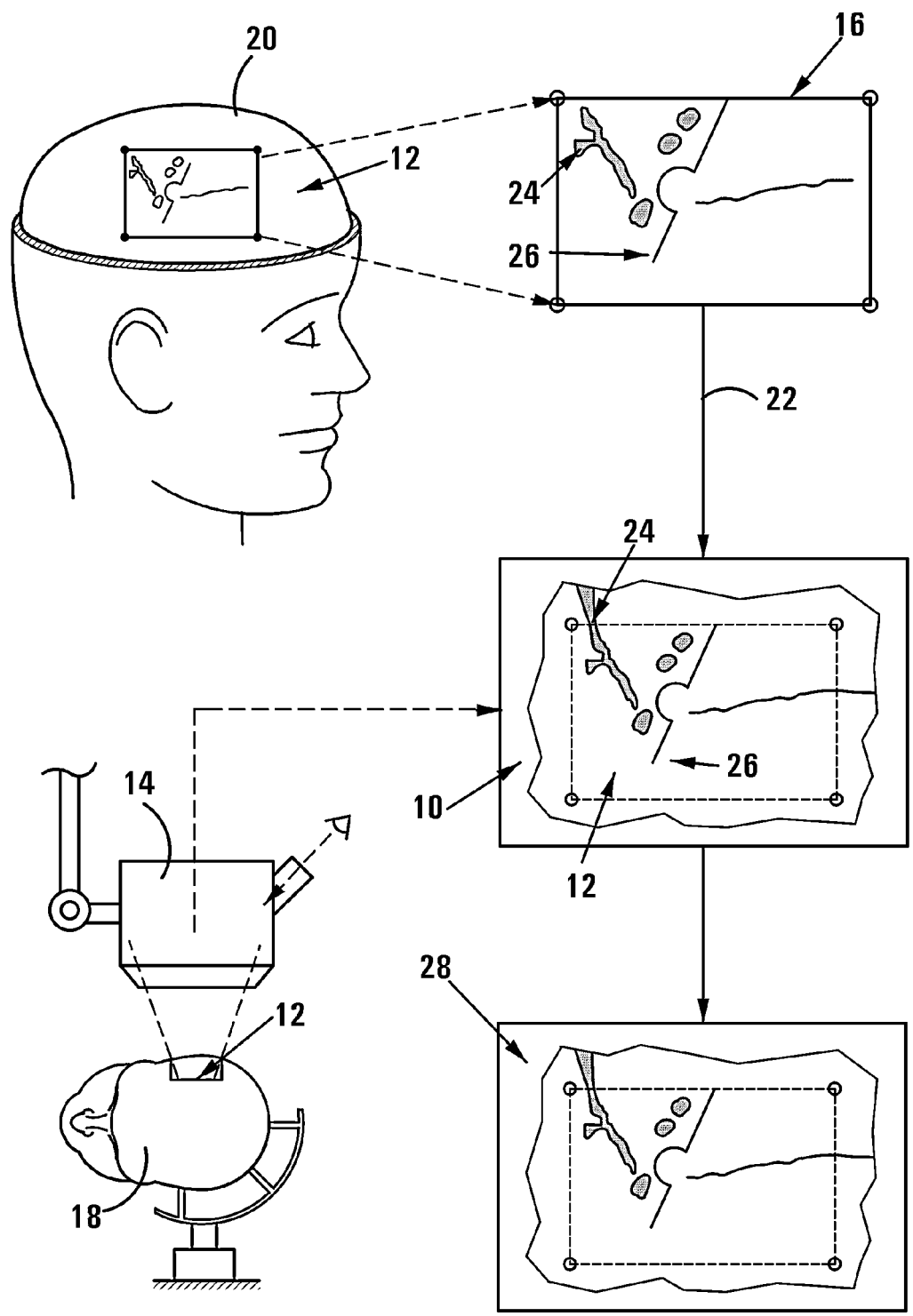
FIG. 1 shows a high level schematic view of the invention in use.

In broad terms, and with particular reference to FIG. 1, in a basic embodiment, the present invention involves obtaining a live optical view 10 of the brain 12 during surgery using, typically, a microscope 14. The invention then involves aligning a functional map 16 for the patient 18, the functional map 16 comprising an anatomical model 20 of the brain 12 and Navigated Brain Stimulation (NBS) functional data for the patient 18, with the live view 10 of the brain 12. This aligning step is indicated schematically by dotted line 22. The patient's NBS functional data would typically have been obtained and compiled prior to surgery, but this aspect will be described in more detail further on in the specification.

In particular, the aligning of the two views 10, 16 is achieved by superimposing anatomical landmarks, such as a vein 24, a sulcus and a gyrus (indicated by single reference numeral 26) from the functional map 16 over the corresponding anatomical landmarks 24, 26 from the live microscope image 10. Once the functional map 16 is aligned with the live view 10, the two views can in effect be glued to each other so as to define an aligned view 28.

Figure 2:
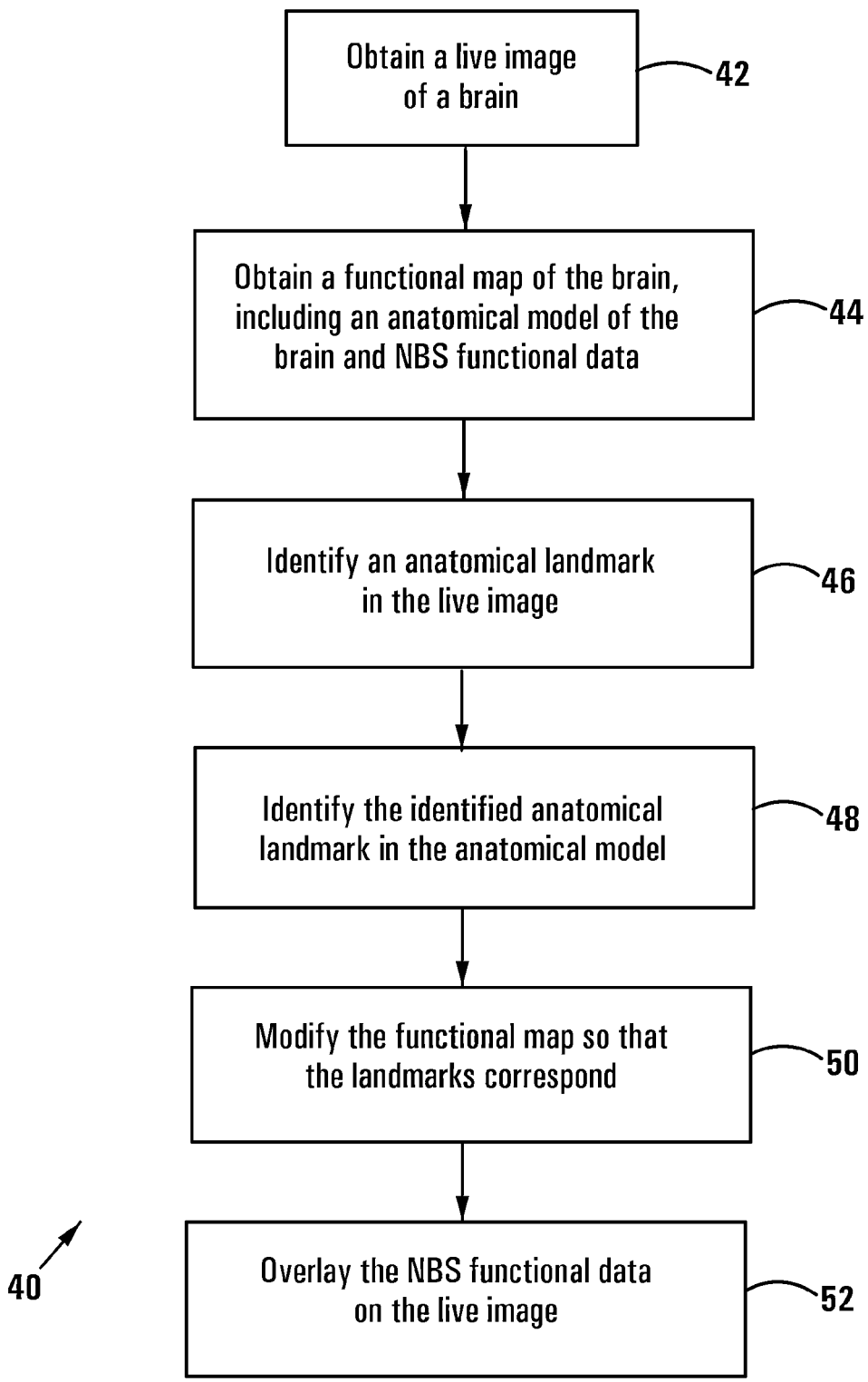
FIG. 2 shows a flow diagram summarizing a method of overlaying NBS functional data on a live image of a brain, according to an embodiment of the present invention.

With reference now to FIG. 2, a method of overlaying NBS functional data on a live image of a brain is indicated by reference numeral 40. The method 40 comprises obtaining a live image of a brain, as indicated by block 42, such as the live image 10 shown in FIG. 1.

Figure 7:
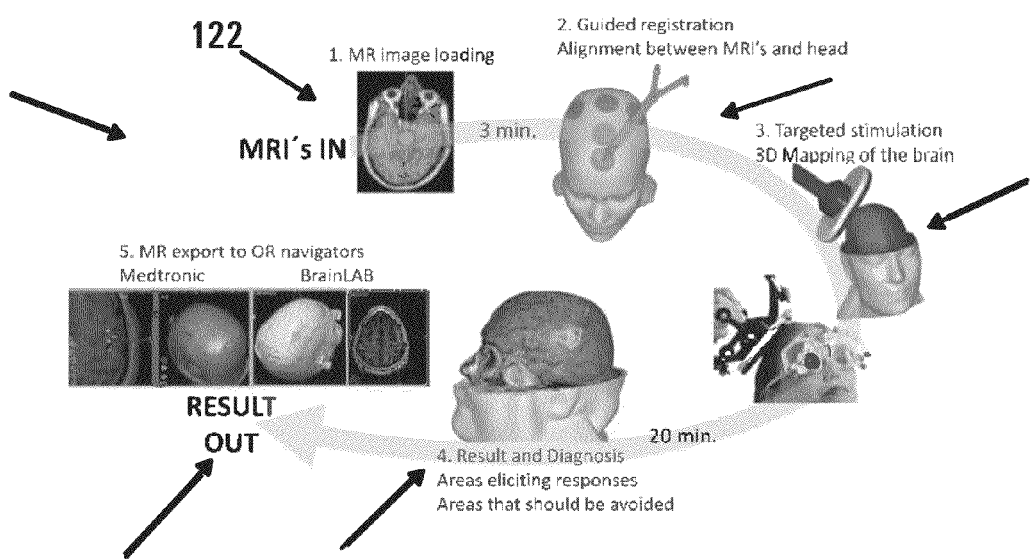
FIGS. 7 to 14 show various pictures and diagrams summarizing various aspects of the present invention in use.

The method 40 further comprises obtaining a functional map of the brain comprising an anatomical model of the brain and NBS functional data associated with the brain, as indicated by block 44. As described above, the functional map would typically have been constructed prior to surgery, using either MRI or CT imaging technology, with the functional map being stored in a database repository for subsequent use during surgery. FIG. 7 shows one way in which a functional map may be constructed. This process 120 comprises loading an MRI image for the patient (arrow 122), and aligning the MRI image with the patient's head (arrow 124). Targeted stimulation enables 3-D mapping of the brain (arrow 126) with the results as to which areas elicited a response (and therefore areas that should be avoided) (arrow 128) being outputted and stored in the database repository (arrow 130).

An advantage of using MRI's is that anatomical landmarks (veins, sulci, gyri, etc.) are readily visible in the image, which is particularly useful during craniotomies, when anatomical landmarks are easily visible by the naked eye. As such, the functional locations tagged during an NBS mapping session can be tagged not only as 3-D locations but also as locations with respect to anatomical landmarks. For example, a motor function of a patient can be tagged at a certain 3-D location based on the orientation of the patient's head. Additionally, or alternatively, the same motor function can be tagged as a certain distance away from, for example, a specific vein and gyrus. Similarly, when the distance between a specific vein and gyrus is known then the motor function can be tagged as, for example, a percentage or fraction of the distance from said vein to said gyrus. As an example, when a surgeon resects cancerous tissue, nearby brain tissue may experience radical compression or stretching due to the brain shift phenomenon. However, typically in such situations anatomical landmarks, such as veins, maintain their relative location to the functional cortex.

This pre-surgical mapping will now be described in more detail with reference to FIG. 3.

Figure 3:
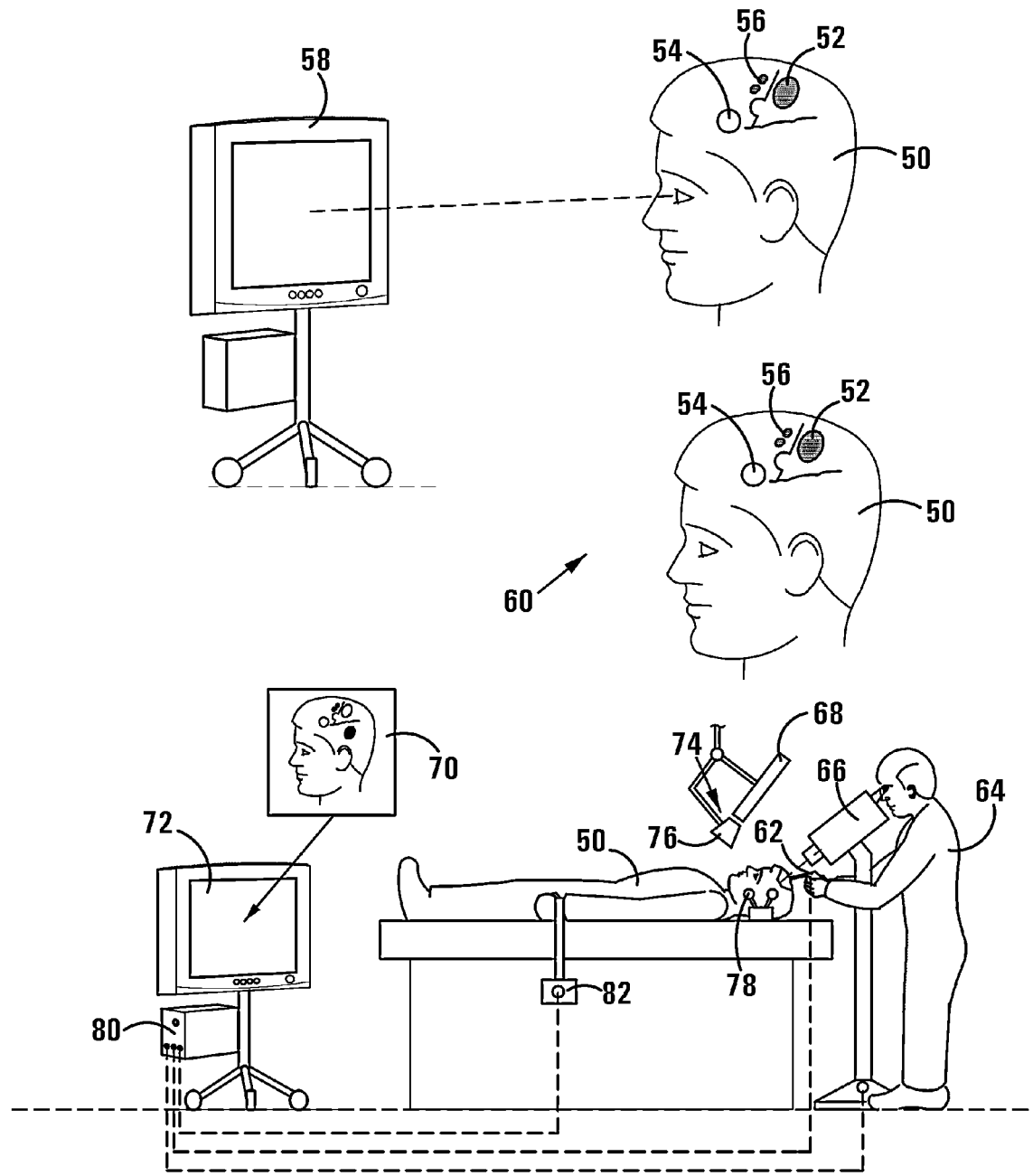
FIG. 3 shows a schematic view of a typical pre-surgical mapping procedure to generate a functional map for a patient, the functional map comprising an anatomical model of the brain and NBS functional data associated with the brain.

As shown in FIG. 3, a patient 50 undergoes a pre-surgical mapping process comprising an NBS guided TMS, the results being measured using electromyography (EMG). In this case, the patient 50 has a tumor 52 close to the Broca's area 54 of the brain, which plays a role in a person's speech. An M1 (distant metastasis) area 56 is also shown. In this particular example, part of the pre-surgical mapping process is speech mapping, during which, for example, the patient 50 is given a task, such as naming objects that appear on a screen 58, and the patients responses before, during and after stimulation are monitored and compared.

After the EMG, the pre-surgical mapping process comprises a pre-surgical planning phase, indicated schematically by arrow 60. During this phase, NBS maps, which are typically 3-D objects, as well as a tumor map, which is typically also a 3-D object, are constructed. This pre-surgical planning phase also comprises determining a trajectory for the surgery.

The pre-surgical mapping process may be double checked at the beginning of surgery by performing a DCS (Direct Cortical Stimulation) procedure to confirm the already recorded functional map obtained above. This may be achieved with a DCS stimulator probe 62 which a surgeon 64 uses on the patient's brain, together with a microscope 66. A screen 68 is provided to enable the patient 50 to name displayed objects, as described above, to facilitate confirmation/verification of the accuracy of the functional mapping process. A view 70 comprising a live view from the microscope 66 and an overlaid functional map is displayed on a screen 72. A tracking system 74 comprising components 76 and 78 is used to ensure the accuracy of the functional map and to enable a 3-D functional map to be constructed. A controller 80 receives inputs from and/or controls various components, such as an EMG input 82, the DCS stimulator probe 62, the microscope 66 and the displays on the screens 68, 70.

Figure 4:
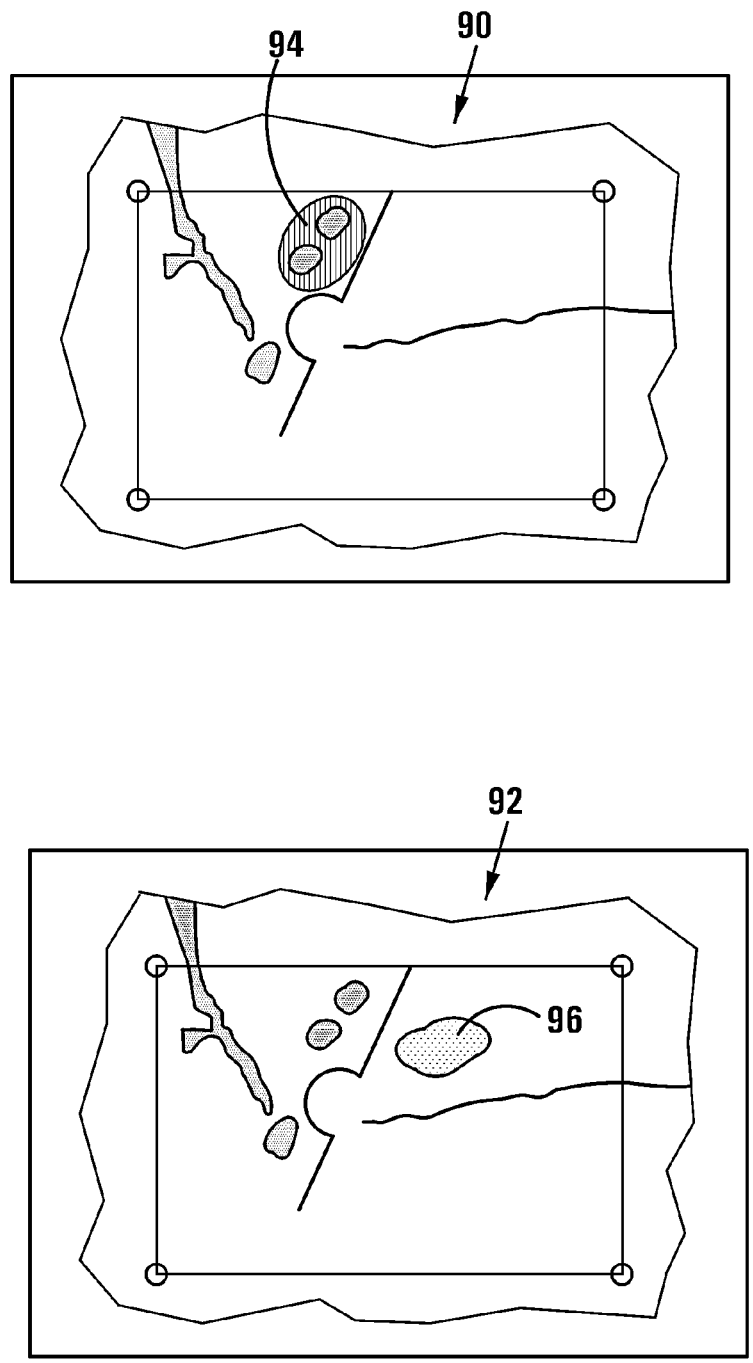
FIG. 4 shows images following a DCS procedure to confirm an already recorded functional map.

FIG. 4 shows images 90, 92 following a DCS procedure to confirm an already recorded functional map. In particular, image 90 shows an area 94 indicated in a different color where the DCS is producing responses. Additional color tools may be provided, such as shown in image 92, in which a tumor 96 becomes visible in fluorescent light after a marker liquid has been injected.

Turning back to FIG. 2, the method 40 further comprises identifying at least one anatomical landmark of the brain from the live image of the brain, as indicated by block 46, and then identifying at least one of said identified anatomical landmarks on the anatomical model of the brain, as indicated by block 48. These steps may take place either manually (i.e. by the surgeon, or an assistant or technician), or automatically by using, for example, optical recognition software to identify, for example, dominant features in the images. The typically landmarks that would be identified (or that the software may be programmed to identify) include veins, sulci and gyri.

The method 40 further comprises modifying the functional map so that the identified at least one anatomical landmark of the model corresponds in size and orientation (i.e. is aligned) to the corresponding at least one anatomical landmark in the live image of the brain, as indicated by block 50. Typically, the step of modifying the functional map includes at least one of the steps of zooming the map in or out, panning, tilting, adjusting, orienting and moving the functional map.

In an embodiment, the modifying step 50 comprises the steps of displaying the functional map and the live image of the brain on a screen (typically on the microscope's screen being viewed by the surgeon), and providing a GUI to enable an operator (either the surgeon or an assistant) to modify the functional map so as to align the identified landmarks.

Alternatively, through the use of, for example, optical recognition software, the orientation and alignment of the two images can be done completely automatically without the involvement of any human interaction. In such an embodiment, the optical recognition software can, for instance, analyze the two images and identify corresponding anatomical landmarks. Once the anatomical landmarks have been identified, alignment software can modify the functional map so that it is correctly aligned with the microscope live image. In such an embodiment, an assistant or technician could be on hand to verify and/or review the final combined image for accuracy.

Figure 5:
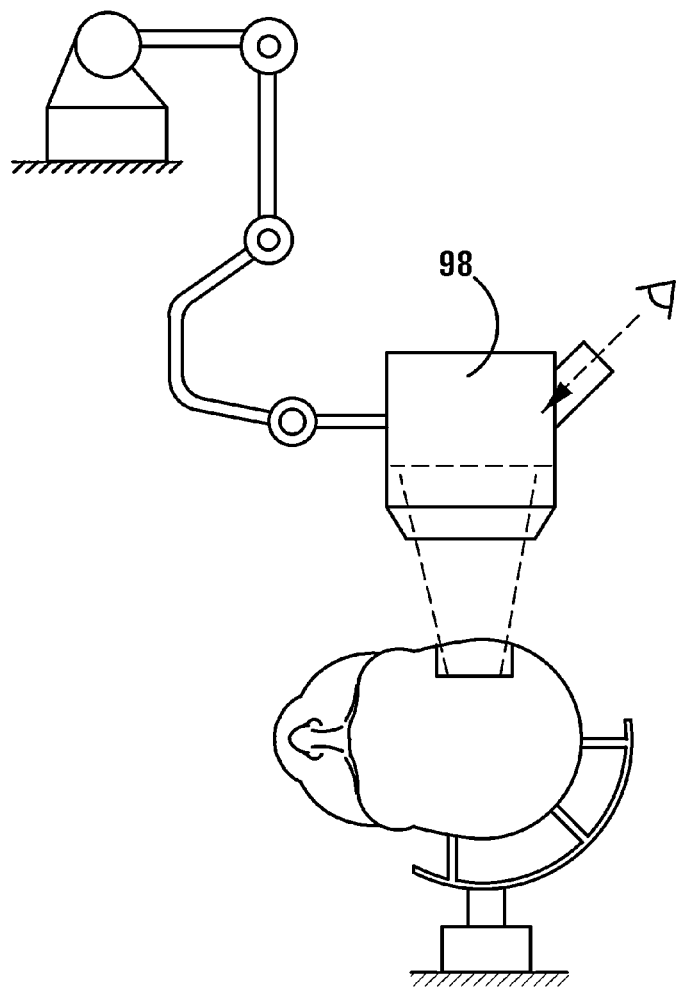
FIG. 5 shows a schematic view of an automated process for aligning a functional map and a corresponding live image.
Figure 6:
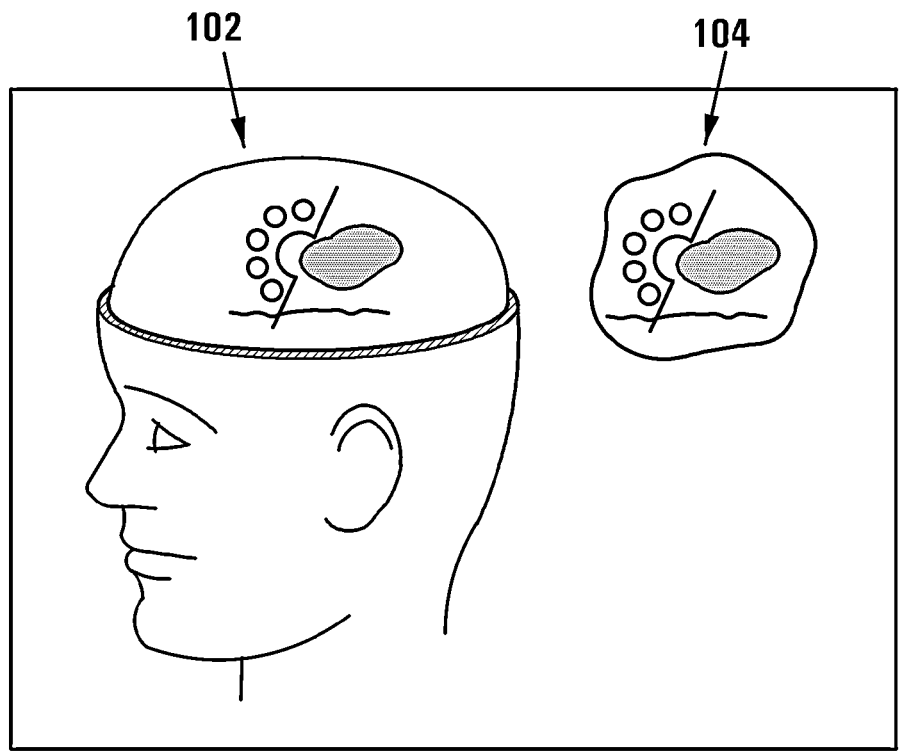
FIG. 6 shows a 3-D export from an NBS procedure, with a segmentation tool allowing an operator to create a required segment to enable an NBS view to be modified and aligned according to a live microscope image.
Figure 6:
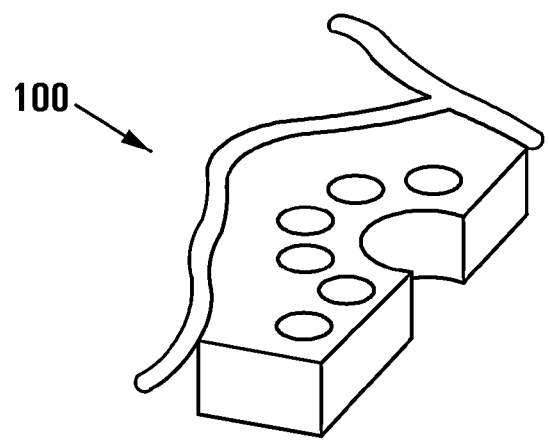

Another option for automated alignment can be scanning, for instance using a scanning laser 98, to scan the skull and craniotomy, as shown in FIG. 5. Shape comparison and/or surface matching between a 3-D functional map, 2-D functional map and/or segmented brain image can then be conducted in order to accurately modify and align the functional map to the microscope image. Other similar methods for partial or fully automated alignment will be recognized by those of ordinary skill in the art without departing from the scope of the present invention. FIG. 6 shows, for example, a 3-D export 100 following from an NBS procedure, with a segmentation tool allowing an operator to create a required segment to enable an NBS view 102 to be modified and aligned according to a live microscope image.

The method 40, as per FIG. 2, may then conclude by digitally overlaying at least the NBS functional data (and in some cases both the anatomical model and the NBS functional data) on the live image of the brain according to the corresponding, aligned anatomical landmarks, as indicated by block 52.

Once the anatomical landmarks are aligned, computer software can effectively lock the two views together. Therefore, and in broad terms, if the microscope moves the functional map will automatically move (or be caused to move) a corresponding amount. Similarly, if the microscope is zoomed in or out the functional map can automatically zoom (or be caused to be zoomed) a corresponding amount. Conversely, if the functional map is adjusted in any way (i.e. zoomed, tilted, rotated etc), then the live image can adjust accordingly to maintain alignment of the images (which may require an adjustment in the orientation of the patient's head and/or the microscope).

The present invention thus envisages a tracking arrangement of sorts, which will now be described in more detail. This tracking feature is important in that during surgery a patient's brain is prone to distortions, such as bloating. Additionally, similar to the heart, a patient's brain is constantly expanding and contracting. Thus, it would be desirable and even necessary to periodically or continuously modify the proportions of the functional map between and/or around the identified anatomical landmarks in response to changes in the actual proportions of the brain matter between and/or around the actual anatomical landmarks. In such an embodiment, a surgeon, or technician, could selectively turn on and off this feature based on the extent of movement/deformation of the brain and/or personal preference.

Following on from the above, although not shown, the method of the present invention, in one embodiment, comprises the steps of continuously tracking the identified anatomical landmarks (as per method step 46 in FIG. 2), which may be done by using a tracking arrangement (which may be similar to the tracking arrangement 74 in FIG. 3) in which the relative position of the microscope with respect to the patient's head is monitored/tracked. Thereafter, this tracking method continuously updates the digitally overlaid NBS functional data to ensure that the identified anatomical landmarks of the functional map remain superimposed/aligned over the corresponding anatomical landmarks of the live image. Thus, as long as the microscope is equipped with a location tracking system or surface scanning sensor, as the microscope moves during the operation the "glued" MRI functional map can move correspondingly.

The method of the invention may comprise the steps of determining a change in distance between at least two anatomical landmarks from the live image, and determining a reliability indication for the location of the NBS functional data based on the determined change in distance. In an embodiment, the reliability indication may be displayed graphically, either by color or by an alphanumerical value. Such a graphical representation can quantify brainshift and provide a reliability indication and/or index of preoperative mapping at any given time point. Such a graphical representation can be toggled on and off at the discretion of a user. Additionally, the software can be set up with an alarm function which alerts an operator that a large enough change in distance has occurred, or is expected to have occurred, such that a surgeon should be aware of possible inaccuracies of the location of the corresponding functional areas.

In addition, or alternatively, the tracking method may comprise the steps of taking a freeze frame from the live image, identifying the anatomical landmarks from said freeze frame, digitally overlaying the modified functional map on the freeze frame, determining any changes between the freeze frame and the live image, and updating the overlay of the at least NBS functional data and the live image based on the determined changes.

The invention may further comprise the step of modifying the transparency of at least a portion of the functional map. In one version, only the transparency of the anatomical model portion of the functional map is adjusted. Thus, the functional data locations on the functional map and the anatomical model themselves can be separate and/or are separable. For example, the anatomical model can be used merely as a guide for the alignment, at which point only the functional data is superimposed on the live microscope view. Furthermore, the transparency of the anatomical model portion of the functional map can be adjusted separately from that of the functional mapping data. Therefore, once the views are aligned, the anatomical model portion of the functional map can be adjusted so that it is barely or nominally visible over the live microscope imaging for periods of the surgery. Additionally, the transparency of the anatomical model portion can be decreased (i.e. making it less transparent) in order to check the alignment of the anatomical landmarks. Similarly, the transparency of the functional data can likewise be adjusted together with, or separately from the anatomical model portion of the functional map.

As previously indicated, at least one (or a combination) of the steps described above is done automatically, typically with the aid of computer software.

According to an embodiment of the invention, the microscope imaging can be sent to a remote location, outside of the operating room. At this location, an assistant, technician and/or automated software can perform the steps of aligning the functional map with the live microscope image and then sending the combined view back to the microscope for display to the surgeon. This arrangement is particularly beneficial in that it reduces the amount of equipment and personnel required in the operating room. While the embodiment herein has been described with the use of an assistant or technician performing the initial alignment, clearly the assistant's or technician's actual interaction can be of any varying degree from complete to non-existent.

The use of anatomical landmarks in aligning the functional map to the live microscope image can alleviate the need for importing NBS functional data to a neuronavigator. By removing the neuronavigator from the process, it is possible to align the NBS data quickly, from a remote non-sterile location, and compensate for brain shift. The present invention also provides for a more accurate and efficient surgical planning tool. As the NBS mapping generates the functional map without the need of a craniotomy, a surgeon can review the functional map during planning to map the best course and even craniotomy location to avoid functional areas. Then, when the surgeon moves into the operating room, s/he is able to see the exact same familiar functional map overlaid on the live microscope image. In an embodiment of the invention, the surgeon is able to annotate and even draw a 3-D course on the functional map such that the annotations and course are displayed in the overlaid combined view. In line with the transparency description above, the surgeon's markups can be selectively displayed with a desired transparency such as with the anatomical model and functional data described.

Although the embodiments described above have been described with respect to a microscope overlay, the same methods and systems can be used when there is any imaging device and a display. For example, a camera can be located in a fixed, or movable, position about the craniotomy and one or more computer displays or TV screens can be located at one or more locations inside or outside of the operating room with the overlaid information.

Furthermore, according to certain embodiments of the present invention, the functional map is a 3-D map. Therefore, if a surgeon is using a means of 3-D (e.g. 3-D display goggles or a 3-D display screen) then the functional map can be interacted with in 3-D space. As an example, the surgeon, during operation or planning, would be able to move through layers of the brain to see what anatomy and functions lay beneath the above surface. Additionally, or alternatively, at a specific depth, or even at the surface, planning or operation software would be able to indicate not only the functional points at the current position but also any functional points located a certain depth from the current position, such as functional points below the current depth but susceptible to interference by a cut at the current depth.

Figure 8:
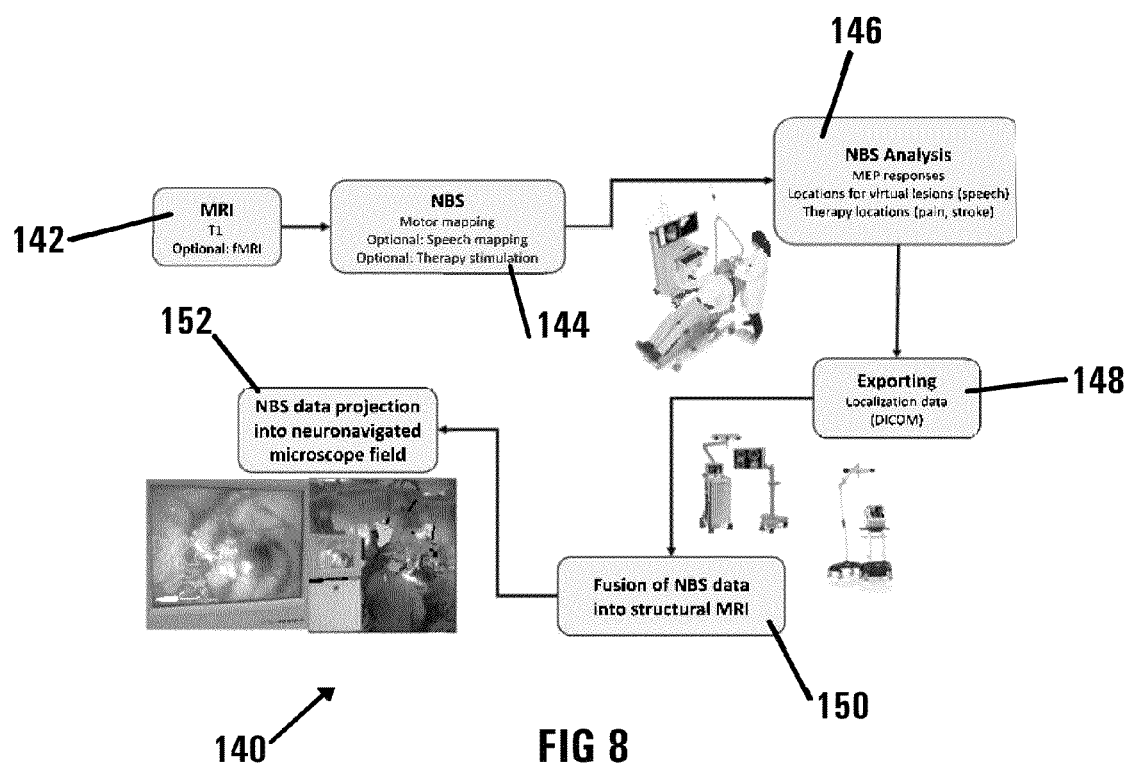
Figure 9:
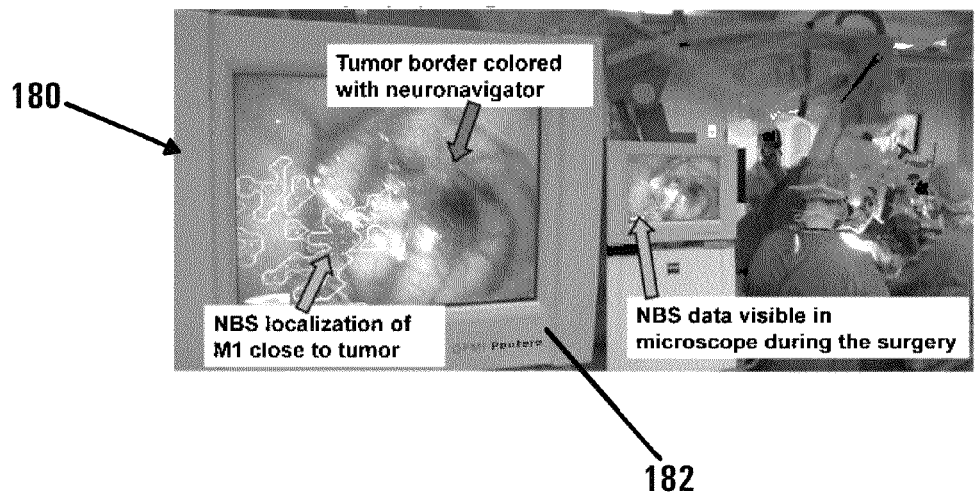
Figure 10:
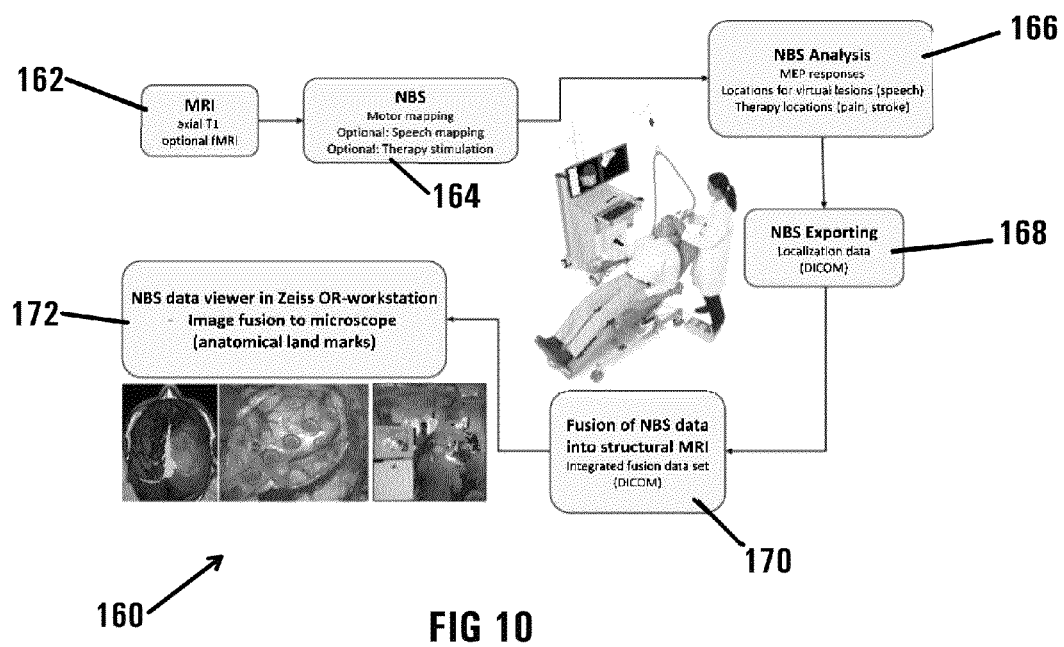

FIGS. 8 to 14 show various pictures and diagrams summarizing various aspects of the present invention in use. FIGS. 8 and 10, for example, show two clinical flows 140, 160, respectively. The flow 140, 160 comprise an MRI step 142, 162, an NBS step 144, 164, NBS Analysis 146, 166, an exporting step 148, 168, the fusion of the NBS data into the MRI functional map 150, 170 and either data projection 152 (as shown in FIG. 8) or display on a workstation 172 (as shown in FIG. 10).

FIG. 9 shows an example of NBS results 180 displayed on a microscope screen 182. In particular, a tumor border is shown relative to an NBS localization of M1 close to the tumor.

Figure 11:
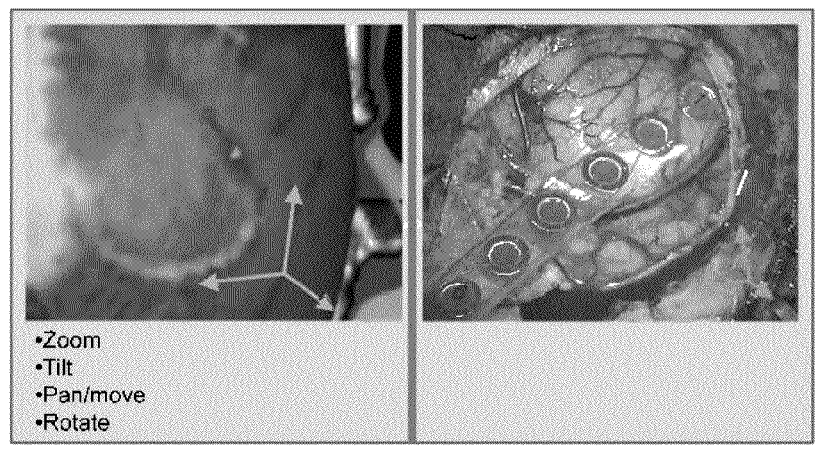

FIG. 11 shows NBS functional data shown on a screen superimposed over a live image of a brain. In particular, this figure shows the ability of modifying the associated functional map by zooming, panning, tilting, adjusting, orienting and/or moving the functional map.

Figure 12:
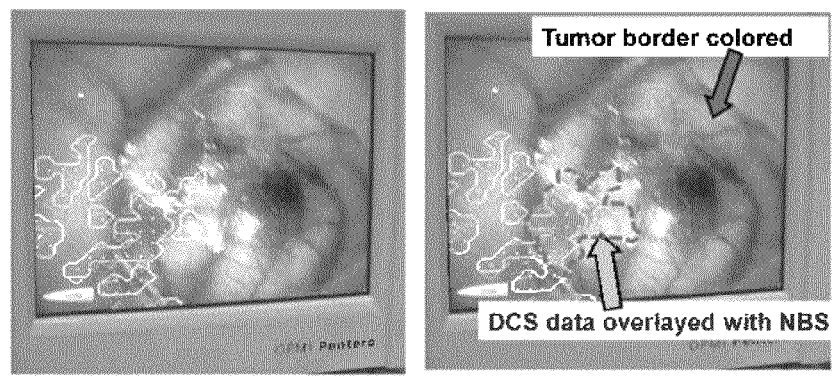

FIG. 12 shows DCS data overlaid with NBS data, which would be used, as described above, to confirm the NBS data.

Figure 13:
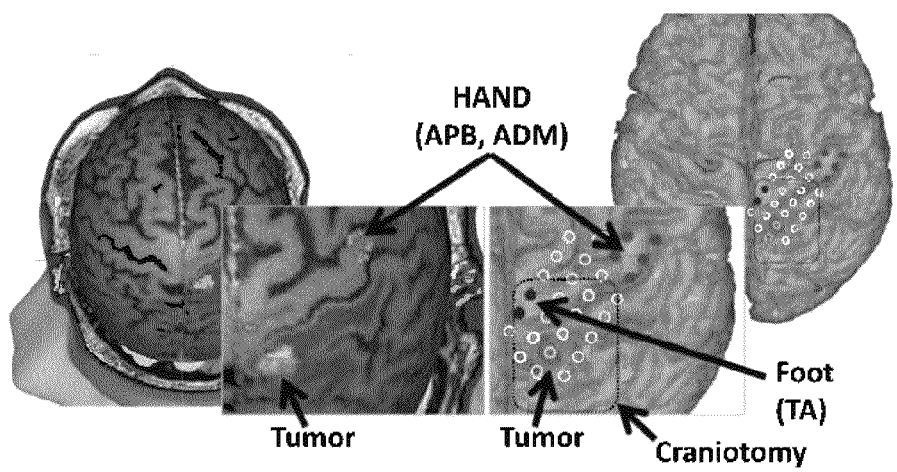

FIG. 13 shows the automatic alignment of NBS functional data with a corresponding live view by using a segmented view, as described above. In this particular case, the preoperative NBS results agreed with intraoperative mapping results made with monopolar intracortical stimulation. The tumor was successfully resected, with motor functions, controlled by an area close to the tumor, working normally after the operation.

Figure 14:
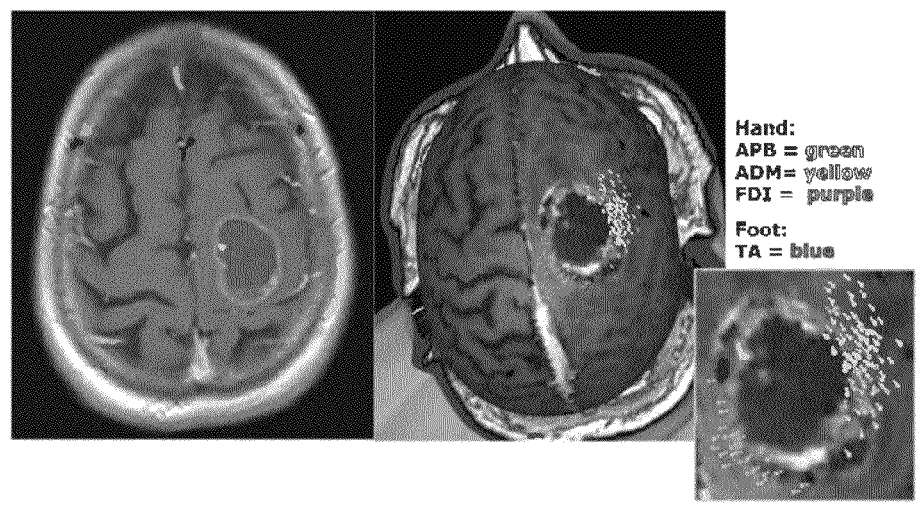

Finally, FIG. 14 shows a pre-operative NBS that yielded surprising results that modified the surgical strategy. Direct cortical stimulation (DCS) was performed intraoperatively. The DCS results were comparable to the preoperative NBS, and the clinical success of the surgery exceeded expectations. This case illustrates that NBS can be used for preoperative mapping in plegic patients. Even more importantly, this case report demonstrates why tumor resection surgery based on NBS may sometimes lead to substantially better clinical outcomes than surgery planned according to fMRI.

The advantage of utilizing anatomical landmarks in functional mapping presents itself during craniotomies when anatomical landmarks are easily visible by the naked eye. As far as the outermost surface of the brain is concerned, a surgeon can readily make out anatomical landmarks and align them with an MRI image regardless of the orientation of the patient's head.

The present invention thus provides a reliable brain mapping solution that avoids accidental motor deficits, thereby increasing patient safety. It also provides the surgeon with accurate data thereby resulting in the confident removal of pathological tissue adjacent to a primary motor cortex. The present invention also reduces the time spent during surgery, thereby further increasing the patient's safety.

When comparing NBS with DCS, NBS is non-invasive whereas DCS is very invasive. NBS is performed pre-surgically (thereby requiring neuro technicians and/or non operating room personnel), whereas DCS requires the patient to be awake. With trained personnel, NBS can take less than 60 minutes (45-60 minutes in most cases, with more challenging cases possibly taking up to 90 Minutes), whereas DCS can take up to 2 hours in an operating room. NBS typically has a 100% success rate, whereas the success rate of DCS is typically between 80-85%. Finally, NBS has no known adverse effects, whereas infection and/or bleeding can occur from DCS.

The invention claimed is:

1. A method of overlaying Navigated Brain Stimulation (NBS) functional data on a live image of a brain, said method comprising the steps of;
    obtaining a live image of a brain,
    obtaining a functional map of the brain comprising an anatomical model of the brain and NBS functional data associated with the brain,
    identifying at least one anatomical landmark of the brain from the live image of the brain,
    identifying at least one of said identified anatomical landmarks on the anatomical model of the brain,
    modifying the functional map so that the identified at least one anatomical landmark of the model corresponds in size and orientation to the corresponding at least one anatomical landmark in the live image of the brain, and
    digitally overlaying at least said NBS functional data on said live image of the brain according to the corresponding, aligned anatomical landmarks.

2. A method according to claim 1, further comprising the steps of;
    continuously tracking said identified anatomical landmarks, and
    continuously updating the digitally overlaid NBS functional data to ensure that the identified anatomical landmarks of the functional map remain superimposed over the corresponding anatomical landmarks of the live image.

3. A method according to claim 1, further comprising the steps of;
    determining a change in distance between at least two anatomical landmarks from the live image, and
    determining a reliability indication for the location of the NBS functional data based on said determined change in distance.

4. A method according to claim 3, further comprising the step of displaying said reliability indication graphically.

5. A method according to claim 1, further comprising the steps of taking a freeze frame from the live image, identifying said anatomical landmarks from said freeze frame, digitally overlaying said modified functional map on said freeze frame, determining any changes between said freeze frame and said live image, and updating the overlay of the at least NBS functional data and the live image based on said determined changes.

6. A method according to claim 1, further comprising the step of modifying the transparency of at least a portion of the functional map.

7. A method according to claim 6, wherein only the transparency of the anatomical model portion of the functional map is adjusted.

8. A method according to claim 1, wherein said modifying the functional map includes at least one of the steps of zooming, panning, tilting, adjusting, orienting and moving.

9. A method according to claim 1, further comprising the steps of;
    displaying the functional map and the live image of the brain on a screen; and
    providing a GUI to enable an operator to modify the functional map so as to align the identified at least one anatomical landmark of the model and the at least one anatomical landmark in the live image of the brain.

10. A method according to claim 1, wherein at least one of the steps is done automatically.

11. A method according to claim 10, wherein a combination of the steps is done automatically.

12. A method according to claim 1, wherein at least one of the steps is done with the aid of computer software.

13. A method according to claim 1, wherein optical recognition software is utilized in any one or more of said steps.

14. A method according to claim 1, wherein the accuracy of at least one of said steps is verified.

15. A method according to claim 14, wherein said verification is done by either a user or automatically using software.

16. A non-transitory computer readable medium having stored thereon a computer program product for causing a processer to perform the steps of;
    identifying at least one anatomical landmark of a brain from a live image of the brain,
    identifying at least one of said identified anatomical landmarks on a functional map of the brain, the functional map comprising an anatomical model of the brain and NBS functional data associated with the brain,
    modifying the functional map so that the identified at least one anatomical landmark of the model corresponds in size and orientation to those of the live image of the brain, and
    digitally overlaying at least said modified NBS functional data on said live image of the brain according to the corresponding, aligned anatomical landmarks.

* * * * *